United States Patent
Kiesel et al.

(10) Patent No.: US 10,064,995 B2
(45) Date of Patent: *Sep. 4, 2018

(54) MONITOR FOR PARTICLE INJECTOR

(71) Applicant: Palo Alto Research Center Incorporated, Palo Alto, CA (US)

(72) Inventors: Peter Kiesel, Palo Alto, CA (US); Joerg Martini, San Francisco, CA (US); Eugene M. Chow, Fremont, CA (US); Scott Uhland, San Jose, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/209,450

(22) Filed: Jul. 13, 2016

(65) Prior Publication Data
US 2016/0317747 A1   Nov. 3, 2016

Related U.S. Application Data

(63) Continuation of application No. 14/246,912, filed on Apr. 7, 2014, now Pat. No. 9,400,174.

(51) Int. Cl.
| | | |
|---|---|---|
| *A61M 5/30* | (2006.01) | |
| *G01N 15/14* | (2006.01) | |
| *G01B 11/14* | (2006.01) | |
| *G01N 15/10* | (2006.01) | |
| *G01N 15/00* | (2006.01) | |
| *A61M 5/20* | (2006.01) | |

(52) U.S. Cl.
CPC ............ *A61M 5/3015* (2013.01); *G01B 11/14* (2013.01); *G01N 15/00* (2013.01);
(Continued)

(58) Field of Classification Search
CPC ....... G01B 11/026; G01S 17/46; G01S 17/89; G01S 7/4972
See application file for complete search history.

(56) References Cited

U.S. PATENT DOCUMENTS

| | | |
|---|---|---|
| 4,037,965 A | 7/1977 | Weiss |
| 4,172,227 A | 10/1979 | Tyrer et al. |

(Continued)

FOREIGN PATENT DOCUMENTS

| | | |
|---|---|---|
| EP | 1950552 | 7/2008 |
| WO | WO0194938 | 12/2001 |
| WO | WO2005017969 | 2/2005 |

OTHER PUBLICATIONS

File History for EP App. No. 15153858.4 as retrieved from the EP Electronic File System on Aug. 5, 2016, 117 pages.
(Continued)

*Primary Examiner* — Sang Nguyen
(74) *Attorney, Agent, or Firm* — Hollingsworth Davis, LLC

(57) ABSTRACT

Approaches for determining the delivery success of a particle, such as a drug particle, are disclosed. A system for monitoring delivery of particles to biological tissue includes a volume, an optical component, a detector, and an analyzer. The volume comprises a space through which a particle can pass in a desired direction. The optical component is configured to provide a measurement light. The detector is positioned to detect light emanating from the particle in response to the measurement light. The detected light is modulated as the particle moves along a detection axis. The detector is configured to generate a time-varying signal in response to the detected light. The analyzer is configured to receive the time-varying signal and determine a delivery success of the particle into a biological tissue based upon characteristics of the time-varying signal.

26 Claims, 11 Drawing Sheets

(52) U.S. Cl.
CPC ....... *G01N 15/1434* (2013.01); *A61M 5/2053* (2013.01); *A61M 2205/3306* (2013.01); *A61M 2210/04* (2013.01); *G01N 2015/0003* (2013.01); *G01N 2015/0046* (2013.01); *G01N 2015/1075* (2013.01); *G01N 2015/1087* (2013.01); *G01N 2015/1093* (2013.01)

(56) References Cited

U.S. PATENT DOCUMENTS

| | | | |
|---|---|---|---|
| 4,441,816 | A | 4/1984 | Hencken et al. |
| 4,596,254 | A * | 6/1986 | Adrian ................ A61B 5/0261 356/28 |
| 5,392,776 | A * | 2/1995 | Thurston ............. A61B 3/1173 600/318 |
| 5,682,038 | A | 10/1997 | Hoffman |
| 5,778,878 | A * | 7/1998 | Kellam ................ A61B 5/0261 600/310 |
| 6,213,579 | B1 | 4/2001 | Cornell et al. |
| 6,649,416 | B1 | 11/2003 | Kauer et al. |
| 6,654,521 | B2 | 11/2003 | Sheng et al. |
| 7,104,634 | B2 | 9/2006 | Weksler et al. |
| 7,291,824 | B2 | 11/2007 | Kiesel et al. |
| 7,358,476 | B2 | 4/2008 | Kiesel et al. |
| 7,386,199 | B2 | 6/2008 | Schmidt et al. |
| 7,420,677 | B2 | 9/2008 | Schmidt et al. |
| 7,471,393 | B2 | 12/2008 | Trainer |
| 7,471,399 | B2 | 12/2008 | Kiesel et al. |
| 7,479,625 | B2 | 1/2009 | Kiesel et al. |
| 7,502,123 | B2 | 3/2009 | Kiesel et al. |
| 7,547,904 | B2 | 6/2009 | Schmidt et al. |
| 7,688,427 | B2 | 3/2010 | Cox et al. |
| 7,701,580 | B2 | 4/2010 | Bassler et al. |
| 7,763,856 | B2 | 7/2010 | Kiesel et al. |
| 7,817,254 | B2 | 10/2010 | Hegyi et al. |
| 7,817,276 | B2 | 10/2010 | Kiesel et al. |
| 7,894,068 | B2 | 2/2011 | Bassler et al. |
| 7,961,326 | B2 | 6/2011 | Martini et al. |
| 8,082,015 | B2 * | 12/2011 | Yodh ................... A61B 5/0059 356/406 |
| 8,153,949 | B2 | 4/2012 | Kiesel et al. |
| 8,153,950 | B2 | 4/2012 | Kiesel et al. |
| 8,203,711 | B2 | 6/2012 | Shinoda |
| 8,373,860 | B2 | 2/2013 | Kiesel et al. |
| 8,388,569 | B2 | 3/2013 | Uhland et al. |
| 8,437,582 | B2 | 5/2013 | Kiesel |
| 8,594,470 | B2 | 11/2013 | Kiesel et al. |
| 8,629,981 | B2 | 1/2014 | Martini et al. |
| 8,723,140 | B2 | 5/2014 | Kiesel et al. |
| 8,821,799 | B2 | 9/2014 | Bassler et al. |
| 8,842,259 | B2 * | 9/2014 | Garey ................... G01C 15/002 356/3.01 |
| 8,921,277 | B2 | 12/2014 | Kiesel et al. |
| 9,029,800 | B2 | 5/2015 | Kiesel et al. |
| 9,074,978 | B2 | 7/2015 | Lo et al. |
| 9,114,606 | B1 | 8/2015 | Ready et al. |
| 9,134,221 | B2 | 9/2015 | Lo et al. |
| 9,164,037 | B2 | 10/2015 | Bassler et al. |
| 9,207,066 | B2 | 12/2015 | Martini et al. |
| 9,261,452 | B2 | 2/2016 | Martini et al. |
| 9,341,562 | B2 | 5/2016 | Martini et al. |
| 2003/0138206 | A1 | 7/2003 | Sheng et al. |
| 2003/0203502 | A1 | 10/2003 | Zenhausern et al. |
| 2003/0235924 | A1 | 12/2003 | Adams et al. |
| 2004/0067137 | A1 | 4/2004 | Moroso |
| 2004/0226386 | A1 | 11/2004 | Gysling et al. |
| 2007/0076210 | A1 | 4/2007 | Kiesel et al. |
| 2007/0145236 | A1 | 6/2007 | Kiesel et al. |
| 2007/0145249 | A1 | 6/2007 | Kiesel et al. |
| 2007/0146704 | A1 | 6/2007 | Schmidt et al. |
| 2007/0146888 | A1 | 6/2007 | Schmidt et al. |
| 2007/0147728 | A1 | 6/2007 | Schmidt et al. |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186504 | A1 | 8/2008 | Kiesel et al. |
| 2008/0197272 | A1 | 8/2008 | Kiesel et al. |
| 2009/0156917 | A1 | 6/2009 | Martini et al. |
| 2009/0190121 | A1 | 7/2009 | Hegyi et al. |
| 2009/0194705 | A1 | 8/2009 | Kiesel et al. |
| 2009/0195773 | A1 | 8/2009 | Kiesel et al. |
| 2010/0155577 | A1 | 6/2010 | Kiesel et al. |
| 2010/0201988 | A1 | 8/2010 | Kiesel et al. |
| 2010/0225913 | A1 | 9/2010 | Trainer |
| 2011/0222062 | A1 | 9/2011 | Martini et al. |
| 2012/0194590 | A1 | 8/2012 | Suzuki |
| 2012/0236291 | A1 | 9/2012 | Pittaro et al. |
| 2012/0271221 | A1 | 10/2012 | Uhland et al. |
| 2013/0016335 | A1 | 1/2013 | Lo et al. |
| 2013/0037726 | A1 | 2/2013 | Kiesel et al. |
| 2013/0037728 | A1 | 2/2013 | Kiesel |
| 2013/0083315 | A1 | 4/2013 | Lo |
| 2014/0152986 | A1 | 6/2014 | Trainer |
| 2014/0192359 | A1 | 7/2014 | Martini |
| 2014/0370612 | A1 | 12/2014 | Kiesel et al. |
| 2015/0105295 | A1 | 4/2015 | Kiesel et al. |
| 2015/0177118 | A1 | 6/2015 | Johnson et al. |
| 2015/0177119 | A1 | 6/2015 | Martini et al. |
| 2015/0185139 | A1 | 7/2015 | Kiesel et al. |
| 2015/0233703 | A1 | 8/2015 | Martini |
| 2015/0233704 | A1 | 8/2015 | Martini et al. |
| 2015/0276387 | A1 | 10/2015 | Kletter |
| 2015/0276486 | A1 | 10/2015 | Martini et al. |
| 2015/0280290 | A1 | 10/2015 | Saha et al. |
| 2015/0285622 | A1 | 10/2015 | Kiesel et al. |

OTHER PUBLICATIONS

Chang et al., Three-dimensional hydrodynamic focusing in two-layer polydimethylsiloxane (PDMS) microchannels, J. Michromech. Microeng 17, 2007, pp. 1479-1486.

Cheong et al., "Flow Visualization and Flow Cytometry with Holographic Video Microscopy", Optics Express 17, 2009, pp. 13071-13079.

Chu et al., "A three-dimensional (3D) particle focusing channel using the positive dielectrophoresis (pDEP) guided by a dielectric structure between two planar electrodes", Lab on a Chip, Issue 5m 2009, pp. 688-691. (abstract only).

Fu et al., "Electrokinetically driven micro flow cytometers with integrated fiber optics for on-line cell/particle detection", Analytica Chimica Acta, Vo. 507 (1), Apr. 2004, pp. 163-169. (abstract only).

Huh et al., "Microfluidics for flow cytometric analysis of cells and particles" Physiol. Meas. 26 (3), Jun. 2005, pp. R73-98. (abstract only).

Ji et al., "Silicon-based microfilters for whole blood cell separation", Biomed Microdevices 10(2), 2008, pp. 251-257. (abstract only).

Kiesel et al., "Spatially Modulated Fluorescence Emission from Moving Particles", Appl. Phys. Lett. 94, 2009, pp. 041107-1-041107-3.

Kiesel et al., "Spatially Modulated Emission Advances Point-of-Care Diagnostics", Laser Focus World, Nov. 2010, pp. 47-50.

Lee, Gwo-Bin et al., "Micromachine-based multi-channel flow cytometers for cell/particle counting and sorting", J. Micromech, Microeng. 15 (2005) 447-454. (abstract only).

Lima et al., "Confocal micro-PIV measurements of three dimensional profiles of cell suspension flow in a square microchannel", Measurement Science and Technology, vol. 17, 2006, pp. 797-808.

Lin et al., "Vertical focusing device utilizing dielectrophoretic force and its application on microflow cytometer", Journal of Microelectromechanical Systems, vol. 13, No. 6, Dec. 2004, 10 pages.

Lindken et al., "Stereoscopic micro particle image velocimetry" Experiments in Fluids, 41, 2006, pp. 161-171.

Pereira et al., "Microscale 3D flow mapping with μDDPIV", Experiments in Fluids, vol. 42 (4), Apr. 2007, pp. 589-599. (abstract only).

Petersson et al., "Free Flow Acoustophoresis: Micorfluidic-Based Mode of Particle and Cell Separation", Anal. Chem, 79 (14), 2007, pp. 5117-5123.

(56) References Cited

OTHER PUBLICATIONS

Pugia et al., "Microfluidic Tool Box as Technology Platform for Hand-Held Diagnostics", Clinical Chemistry, vol. 51 (10), 2005, pp. 1923-1932.
Schrum et al., "Microchip Flow Cytometry Using Electrokinetic Focusing", Anal. Chem. 71 (19), Oct. 1999, pp. 4173-4177. (abstract only).
Sheng et al., "Digital holographic microscope for measuring three-dimensional particle distributions and motions", Applied Optics, Vo. 45 (16), Jun. 2006, pp. 3893-3901.
Yamada et al., "Pinched flow fractionation: continuous size separation of particles utilizing a laminar flow profile in a pinched microchannel", Anal. Chem. 76 (18), Sep. 2004, pp. 5465-5471. (abstract only).
Yamada et al., "Microfluidic Particle Sorter Employing Flow Splitting and Recombining", Anal. Chem. 78, 2006, pp. 1357-1362.
Zhu et al., "Dielectrophoretic focusing of particles in a microchannel constriction using DC-biased AC flectric fields", Electrophoresis, vol. 30 (15), Jul. 2009. (abstract only).
File History for U.S. Appl. No. 14/246,893.
File History for U.S. Appl. No. 14/246,912.
File History for U.S. Appl. No. 14/181,560.
File History for U.S. Appl. No. 14/181,524.
File History for U.S. Appl. No. 14/181,571.
File History for U.S. Appl. No. 14/181,530.

\* cited by examiner

MONITOR FOR PARTICLE INJECTOR

RELATED APPLICATIONS

This application is a continuation of U.S. Ser. No. 14/246,912 filed Apr. 7, 2014, which is incorporated herein by reference in its entirety.

TECHNICAL FIELD

This disclosure relates generally to techniques for performing system and sample analysis by evaluating light emanating from the one or more particles in a particle delivery system. More particularly, the application relates to techniques for monitoring and controlling delivery of drug particles, and to components, devices, systems, and methods pertaining to such techniques.

BACKGROUND

The present disclosure relates generally to techniques that determine object characteristics using light emanating from the particles. More specifically, the techniques can use filter and/or optical arrangements to allow for the transmission, reflection, fluorescence, phosphorescence, photoluminescence, chemoluminescence and/or scattering of light with time variation, such as where the particles are moving relative to the filter and/or optical arrangements.

Various techniques have been proposed for using light emanating from objects. For example, U.S. Pat. No. 7,358,476 (Kiesel et al.) describes a fluidic structure with a channel along which is a series of sensing components to obtain information about objects traveling within the channel, such as droplets, cells, viruses, microorganisms, microparticles, nanoparticles, or other objects carried by fluid. A sensing component includes a set of cells that photosense a range of photon energies that emanate from objects. A processor can receive information about objects from the sensing components and use it to obtain spectral information. Additional techniques are described, for example, in U.S. Patent Application Publications 2008/0181827 (Bassler et al.) and 2008/0183418 (Bassler et al.), and in U.S. Pat. No. 7,547,904 (Schmidt et al.), U.S. Pat. No. 7,420,677 (Schmidt et al.), U.S. Pat. No. 7,701,580 (Bassler et al.), U.S. Pat. No. 7,894,068 (Bassler et al.), U.S. Pat. No. 8,373,860 (Kiesel et al.), and U.S. Pat. No. 7,386,199 (Schmidt et al.).

SUMMARY

According to one embodiment, an assembly for delivering and monitoring delivery of particles to biological tissue includes a delivery device, a volume, a spatial filter with mask features, a detector, and an analyzer. The delivery device is configured to contain a particle and accelerate the particle in a desired direction. The volume comprises a space through which the particle can pass. The detector is positioned to detect light emanating from the particle along a detection region within the volume. The detected light is modulated according to the mask features as the particle moves along the detection region. The detector is configured to generate a time-varying signal in response to the detected light. The analyzer is configured to receive the time-varying signal and determine a delivery success of the particle into a biological tissue based upon characteristics of the time-varying signal.

In another embodiment, a system for monitoring delivery of particles to biological tissue includes a volume, an optical component, a detector, and an analyzer. The volume comprises a space through which a particle can pass in a desired direction. The optical component is configured to provide a measurement light. The detector is positioned to detect light emanating from the particle in response to the measurement light. The detected light is modulated as the particle moves along a detection region. The detector is configured to generate a time-varying signal in response to the detected light. The analyzer is configured to receive the time-varying signal and determine a delivery success of the particle into a biological tissue based upon characteristics of the time-varying signal.

Some embodiments involve a method of monitoring delivery particles to biological tissue including passing a particle through a volume that includes a biological tissue disposed adjacent thereto, detecting a light from the particle moving through the volume relative to a spatial filter, generating a time-varying signal in response to the detected light, and analyzing the signal to determine a delivery success of the particle into the biological tissue based upon characteristics of the time-varying signal.

Another embodiment includes a method of transcutaneous drug delivery including propelling particles individually or a few at a time from a delivery device, passing the particles through a volume, detecting a light from the particles moving through the volume, generating a time-varying signal in response to the detected light, analyzing the time-varying signal to determine a delivery success of the particles at penetration into a biological tissue, iteratively adjusting delivery characteristics of the particles based on the analysis until a predetermined success rate is achieved, and delivering the drug in a bolus of many particles using the adjusted delivery characteristics.

In yet a further embodiment, a system for determining one or more properties of a material includes a volume through which a particle can pass in a desired direction, an optical component, a detector, and an analyzer. The optical component is configured to provide a measurement light. The detector is positioned to detect light emanating from the particle in response to the measurement light. The detected light is modulated as the particle moves along a detection region within the volume. The detector is configured to generate a time-varying signal in response to the detected light. The analyzer is configured to receive the time-varying signal and determine one or more properties of the material based upon characteristics of the time-varying signal.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
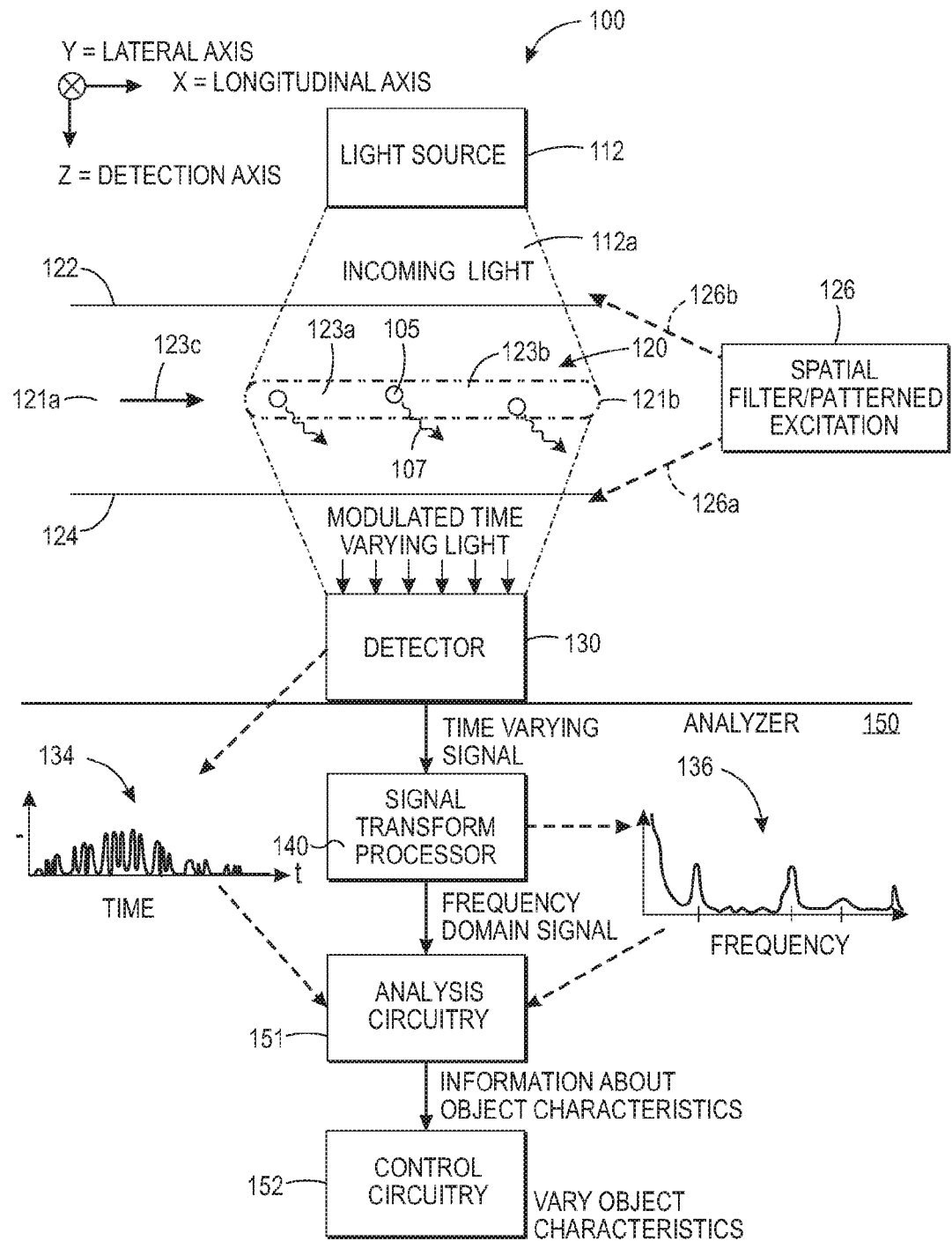
FIG. 1 is an example embodiment of an assembly with a detector and an analyzer configured to determine particle characteristics based on spatially modulated light.

Healthcare is a rapidly expanding sector of the United States and world economies. Drug delivery is a subsector of the healthcare industry that can benefit from technological advance. Needles, although effective, lead to severe issues such as pain, needle phobia, and accidental needle sticks. Hence, there is a strong interest from the patients, healthcare providers, and drug manufacturers to develop needle-free methods of drug delivery. One such needle-free method of drug delivery is disclosed in United States Patent Application Publication 2012/0271221 A1 (Uhland et al.), entitled "Delivery Devices and Methods with Collimated Gas Stream and Particle Source", the disclosure of which is incorporated herein by reference in its entirety. That application describes the use of super-sonic jets of particles, as described in ballistic aerosol marking, for controlled delivery of therapeutic particles across the skin.

The permeability of skin for drug particles depends on various characteristics of both the skin and the drug particles. For example, the delivery speed and size of the drug particles can affect the chances of delivery through the skin. Additionally, skin permeability varies from person to person and can vary with body location, skin temperature and health condition (e.g., sweating, fever). Considering these and other factors that can impact drug delivery success, a monitoring device that allows for monitoring the success of delivery (i.e. determine if the particle(s) have been injected) is desirable.

This disclosure describes a monitoring device and related techniques, methods, systems, and apparatuses that can be used to monitor the success of particle injection by distinguishing between a delivery path and a reflected path (if it exists) for each particle passing through a volume. The application describes analysis techniques and an analyzer that can be used to measure characteristics of incoming and potentially reflected particles such as a speed (both incoming and reflected), particle size, particle location and trajectory, and particle material properties based upon time-varying signals. In some instances, the analyzer can additionally be configured to analyze properties of a biological tissue such as opacity, temperature, moisture content, etc. In some embodiments, a control circuitry can be configured to vary one or more of the characteristics of delivery of the particle based upon one or more of analyzed properties of the biological tissue and one or more characteristics of the reflected path.

Various techniques have been proposed for using light emanating from objects. These techniques have been functionalized for various applications and are generally effective for recognizing and obtaining object characteristics such as size, speed, charge, porosity, surface characteristics, elasticity, and material composition for particular analytes. Light emanating from an object can originate from a multitude of physical processes including: Fluorescence, scattering, up-conversion, second harmonic generation, multi-photon excited fluorescence, Raman scattering, phosphorescence, absorption etc.

The embodiments described herein can be used to perform a size (in three dimensions), position and/or movement analysis on a drug particle during the delivery path, and if delivery is not successfully accomplished, can perform a similar analysis on the drug particle moving along the reflected path. These determinations are based on spatially modulated light emanating from the particle. The approaches described can aid in the analysis and delivery of drug particles to biological tissue including living skin, as well as dead tissue (e.g., a food product). Thus, the term biological tissue is used broadly to refer to biological cells, whether living or dead at the time of analysis. A "patient" can be a human, an animal, or a food product. In some applications, the techniques, systems, and apparatuses described can be used on non-biological material to measure and modify properties of the material (e.g., cause material hardening, change certain optical properties, inject dyes, etc.).

It will be understood that the techniques, apparatuses, systems, and methods described herein are applicable to detect various particles such as analytes present in a sample. As used herein the term "particle" refers broadly to any object or objects of interest to be detected and is not limited to a drug used for therapeutic purposes. The particle can refer to one or more test particles, and additionally, can refer to one or more particles delivered for the intended purpose (e.g., therapy). Thus, particle can refer to one or more test particles adapted to test the properties of the biological tissue and optimize drug delivery characteristics. These test particles can be one or more drug particles from a group of particles intended to be delivered as the drug in a bolus of many particles or can be one or more beads (e.g. micrometer sized plastic particles) having characteristics such as size, trajectory, and speed intended to simulate the characteristics of the group of particles intended to be delivered as the drug in a bolus of many particles. In some applications, a particle of interest is an object(s) or analyte(s) that is relatively small, and may be microscopic in size. The particles may be dry (have a low moisture content) or may be comprised of droplets. A given particle may be or include one or a collection of biological cell(s), virus(es), molecule(s), proteins or protein chains, DNA or RNA fragments, sub-molecular complex(es), emulsions, microparticles, nanoparticles, beads or other small particles that can bind and carry specific chemicals or other analytes.

In some embodiments, one or more sensors can obtain information about the particle by receiving a signal(s) therefrom; for example, the signal in the form of light can emanate from the particle, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a sensor such as a photodetector. Cells or other particles may be treated, e.g., stained or tagged with a suitable fluorescent probe or other agent, in such a way that they emit light or absorb light in a predictable fashion when illuminated with excitation light. In this regard, the light emitted by a given excited particle may be fluorescent in nature, or it may constitute a form of scattered light such as in the case of elastic or inelastic (Raman) scattering. For simplicity, the light that emanates (by e.g., scattering, emission, or transmission) from a particle is referred to herein as "emanating light" "light emanating" or simply as "light" in some circumstances. Similarly, the light that emanates from a light source can be referred to as "excitation light" or "measurement light" herein. It will be understood that the techniques, assemblies, apparatuses, systems, and methods described herein are applicable to detecting all forms of light emanating from a particle or constituent parts thereof.

The embodiments described herein utilize various techniques and spatial filters disclosed in one or more of the Applicants' co-filed applications, application Ser. No. 14/181,560, entitled "Spatial Modulation of Light to Determine Object Position", application Ser. No. 14/181,524, entitled "Spatial Modulation of Light to Determine Dimensional Characteristics of Objects in an Injection Direction", application Ser. No. 14/181,571, entitled "Determination of Color Characteristics of Objects Using Spatially Modulated Light", and application Ser. No. 14/181,530, entitled "Spatial Modulation of Light to Determine Object Length", co-pending herewith. These co-pending applications are herein incorporated by reference in their entirety. In view of the teachings of these co-pending applications, it is possible to determine one or more characteristics of the delivery of the particle including a speed of the particle during the delivery path, a size of the particle in one or more of three dimensions, and a three dimensional position of the particle within a volume during the delivery path. Additionally, one can determine one or more characteristics of the reflected path of the particle, should one occur. The one or more characteristics of the reflected path include a speed of the particle during the reflected path and three dimensional position of the particle within the volume during the reflected path.

The three dimensional position of the particle within the volume can include a determination of a depth of the particle along a detection axis (also sometimes referred to as a depth axis), multidimensional position and/or multidimensional trajectory of the particle traveling along both the delivery and reflected paths. The techniques and embodiments disclosed can be used to determine particle lateral position referenced to a lateral axis, and particle travel position along one or both of the delivery path and the reflected path referenced to a longitudinal axis. Additionally, as the particle travels in time within the volume, additional information can be obtained including trajectory information such as angles of travel in three dimensions and particle speed. In further embodiments, the techniques and embodiments disclosed can be used to determine particle length along the longitudinal axis (x-axis) parallel to a general injection direction, particle width along the lateral axis (y-axis) perpendicular to the general injection direction, and/or particle thickness along the depth axis (z-axis) generally perpendicular to the general injection direction.

The embodiments described herein involve the use of at least one spatial mask or optically induced excitation that can be deployed in a variety of drug delivery applications, including analysis of system properties and/or detection of various characteristics of one or more particles in a sample. As each particle moves along an injection direction, the particle emanates light that is spatially modulated or otherwise patterned and detected by a detector. The detector generates a time-varying signal in response to the sensed patterned light emanating from the particle. In some implementations, a non-imaging or non-pixilated photodetector can be used to generate the time-varying signal based on the patterned light. The use of a non-imaging photodetector may enhance compatibility with high-throughput particle analysis.

The time-varying signal includes information about the particle's characteristics (e.g., size, movement, and relative position). In some embodiments, the time-varying signal can be analyzed in the time domain to extract the desired information regarding the particle. For example, the time-varying signal may be compared or correlated to a known template signal and/or the time-varying signal may be analyzed by examining various morphological and durational characteristics of the time-varying signal. In some embodiments, the time-varying signal may be transformed from the time domain to the frequency domain and the analysis may be carried out on the frequency domain signal.

FIG. 1 is an example of an assembly 100 configured to determine particle characteristics based on spatially modulated light. The assembly 100 includes a light source 112, a mask, e.g., a spatial filter 126, a volume 120, a detector 130, a signal processor 140, and an analyzer 150. Components of the assembly are arranged in a coordinate system that includes a longitudinal axis, designated as the x-axis herein, a lateral axis, designated as the y-axis, and a depth axis, designated as the z-axis. In the description below, the injection direction is selected to lie generally along the longitudinal axis of the coordinate system, and the longitudinal, lateral, and depth axes are orthogonal to one another. Those skilled in the art will appreciate that any coordinate system could alternatively be selected, the arrangement of the assembly with respect to the coordinate system is arbitrary and does not change the operation of the assembly, and that non-orthogonal axis systems could alternatively be used.

The volume 120 is adapted to receive a sample of interest to be analyzed. The sample may enter the volume 120 at an inlet 121a thereof and exit the volume 120 at an outlet 121b thereof, moving generally along the x-direction through a volume 120 formed between confining members 122, 124. The members 122, 124 may be or comprise a housing wall constructed of suitable material (e.g., glass, plastic, or other suitable materials). The members 122, 124 need not, however, be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122, 124 may be omitted. At least a portion of the confining member 122 is transmissive to excitation light emitted by the light source 112 at least in an excitation region 123*a*. In that regard, the light source 112 may emit excitation light 112*a* towards the volume 120.

In some cases, the light source 112 may comprise a conventional laser, laser diode, light emitting diode (LED) source or a resonant cavity LED (RC-LED) source, for example. If desired, the light source may incorporate one or more filters to narrow or otherwise tailor the spectrum of the resultant output light. Whichever type of light source is selected, the spectral makeup or composition of the excitation light emitted by the light source 112 is preferably tailored to excite, scatter, or otherwise cause emanation of light from at least some of the objects that may be present in the sample, as discussed further below.

The sample is depicted as containing particles 105 that emanate light 107 in all directions (only some directions are illustrated). The particles 105 may have a variety of characteristics, some of which can be determined by the analyzer 150 based on the emanating light 107.

The detector 130 receives time-varying light and generates an electrical signal in response to the time-varying light. The time variation in the light detected by the detector 130 may be the result of interaction between the excitation light and an input spatial filter to create spatially patterned excitation light that illuminates the particle 105. Alternatively, the time variation in the light detected by the detector 130 may be the result of interaction between light emanating from the particles 105 and an output spatial filter. In yet other embodiments, the time variation in the light detected by the detector 130 may be the result of patterned excitation light using optical components such as micro-optics.

In some embodiments, the detector 130 includes an optical filter arranged between the detector and the objects. An optical filter can be particularly useful when the emanating light is fluorescent light and the optical filter is configured to substantially block the wavelengths of the excitation light and to substantially pass the wavelengths of the light emanating from the objects.

The assembly 100 of FIG. 1 includes the spatial filter 126 (sometimes referred to as a mask) and/or patterned excitation light which can be positioned in various locations. Dashed arrows 126*a* and 126*b* indicate possible locations of the spatial filter 126 and/or patterned excitation light to provide spatially modulated light and/or modulated excitation light.

In some configurations, indicated by arrow 126*a*, the spatial filter can be disposed between the volume 120 and the detector 130. In this position, the spatial filter is referred to as an output spatial mask. In other configurations, indicated by arrow 126*b*, the spatial filter can be disposed between the light source 112 and the volume 120. In this position, the spatial filter is referred to as an input spatial filter. An input spatial filter may be adapted to transmit light emitted by the light source by varying amounts along the excitation region 123*a* of the volume 120. In this configuration, the input spatial filter creates patterned excitation light in the excitation region 123*a* of the volume 120. According to various implementations, an input spatial filter may comprise a physical mask including a sequence or pattern of first regions that have a first optical characteristic, e.g., are more light transmissive, and second regions that have a second optical characteristic, different from the first characteristic, e.g., are less light transmissive. Alternatively or in addition to a spatial filter, one or more optical components such as micro-optics or a patterned light source configured to create the excitation pattern can be utilized. The excitation pattern can be imaged and/or directed onto the excitation region 123*a* using additional optical components for the imaging (e.g., lenses) and/or direction, (e.g., fiber optics or waveguides).

In some embodiments, an output spatial filter may be utilized and disposed between the particles 105 and the detector 130 at a detection region 123*b* of the volume 120. In some embodiments, the excitation region 123*a* and the detection region 123*b* overlap. In other embodiments, there may be partial overlap between the excitation and detection regions or the excitation and detection regions may be non-overlapping or multiple detection regions and/or excitation regions may be used with various overlapping and/or non-overlapping arrangements. In the assembly 100 shown in FIG. 1, the output spatial filter may be adapted to interact with the light 107 emanating from the particles 105 in the volume 120. In some embodiments, the output spatial filter may be a physical mask comprising a sequence or pattern of first regions that are more light transmissive and second regions that are less light transmissive. In some embodiments, color spatial filters may be used such that a first region of the color spatial filter is more transmissive to a first wavelength band and less transmissive to a second wavelength band and a second region of the color spatial filter is less transmissive to the first wavelength band and is more transmissive to the second wavelength band.

According to some embodiments of an assembly 100 that include an input spatial filter, as the particle 105 travels in the injection direction 123*c* in the excitation region 123*a* of the volume 120, light emanating from the light source 112 is alternately substantially transmitted to the particle 105 and substantially blocked or partially blocked from reaching the particle 105 as the particle 105 travels along the injection direction 123*c*. The alternate transmission and non-transmission (or reduced transmission) of the excitation light 112*a* along the injection direction 123*c* produces time-varying light 107 emanating from the particle 105. The time-varying light 107 emanating from the particle 105 falls on the detector 130 and, in response, the detector 130 generates a time-varying detector output signal 134.

According to some embodiments of the assembly 100 that include the output spatial filter configuration, light 112*a* from the light source 112 illuminates the particle 105, causing the particle 105 to emanate light 107. As the particle 105 travels in the injection direction 123*c* in the detection region 123*b* of the volume 120, the output spatial filter alternatively entirely or substantially blocks the light 107 emanating from the particle 105 from reaching the detector 130 and substantially transmits the light 107 emanating from the particle 105 to the detector 130. The alternate substantial transmission and blocking (or partial blocking) of the light 107 emanating from the particle 105 as the particle 105 flows through the detection region 123*b* produces time-varying light that falls on the detector 130. In response, the detector 130 generates the time-varying detector output signal 134.

In some embodiments such as the embodiment of FIG. 1, the analyzer 150 may include a signal transform processor 140 that converts the time-varying detector output signal 134 to a frequency domain output signal 136 so as to provide spectral power as a function of frequency. The signal transform processor 140 is shown as part of the analyzer 150 in this embodiment, but may be part of the detector in some embodiments or may comprise separate circuitry in other embodiments. For example, in some embodiments, the signal transform processor may be part of the analyzer circuitry along with the detector.

For conversion, the signal processor 140 may use known techniques such as discrete Fourier transform including, for example, a Fast Fourier Transform "FFT" algorithm. Thus, the frequency domain output signal 136 represents the frequency component magnitude of the time-varying detector output signal 134, where the frequency component magnitude is the amount of a given frequency component that is present in the time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of the time-varying signal 134. However, other methods or techniques of representing the frequency component magnitude, or other measures of the frequency component magnitude, may also be used. Examples may include e.g. the square root of the Fourier signal power, or the signal strength (e.g. as measured in voltage or current) obtained from a filter that receives as input the time-varying detector output signal 134.

In FIG. 1, the time-varying detector output signal 134 and/or the frequency domain detector output signal 136 can be passed to the analysis circuitry 151 of the analyzer 150. The analysis circuitry 151 is configured to receive the time-varying detector output signal 134 and/or the frequency domain detector output signal 136 and to determine one or more characteristics of delivery of the particle 105 and the injection success based upon the time-varying detector output signal 134 and/or the frequency domain detector output signal 136. In yet further embodiments, the analysis circuitry 151 can additionally be configured to analyze and determine properties of a biological tissue.

As will be discussed subsequently, the various embodiments discussed herein provide examples of techniques for determining the one or more characteristics of delivery of the particle 105 and the injection success using various mask designs and processing techniques. As used herein, the depth of the particle 105 is a distance of the particle 105 within the volume 120 as measured along the z-direction of the Cartesian coordinate system of FIG. 1. Thus, the depth is a distance generally perpendicular to the injection direction 123c along the volume 120. In some embodiments, the depth can be measured relative to a component such as the filter or one of the confining members.

In some embodiments, a control circuitry 152 can be configured to vary one or more of the characteristics of delivery of the particle 105 based upon one or more of the analyzed properties of the biological tissue and one or more characteristics of the reflected path of the particle 105 back into the volume 120 from the biological tissue.

Figure 2:
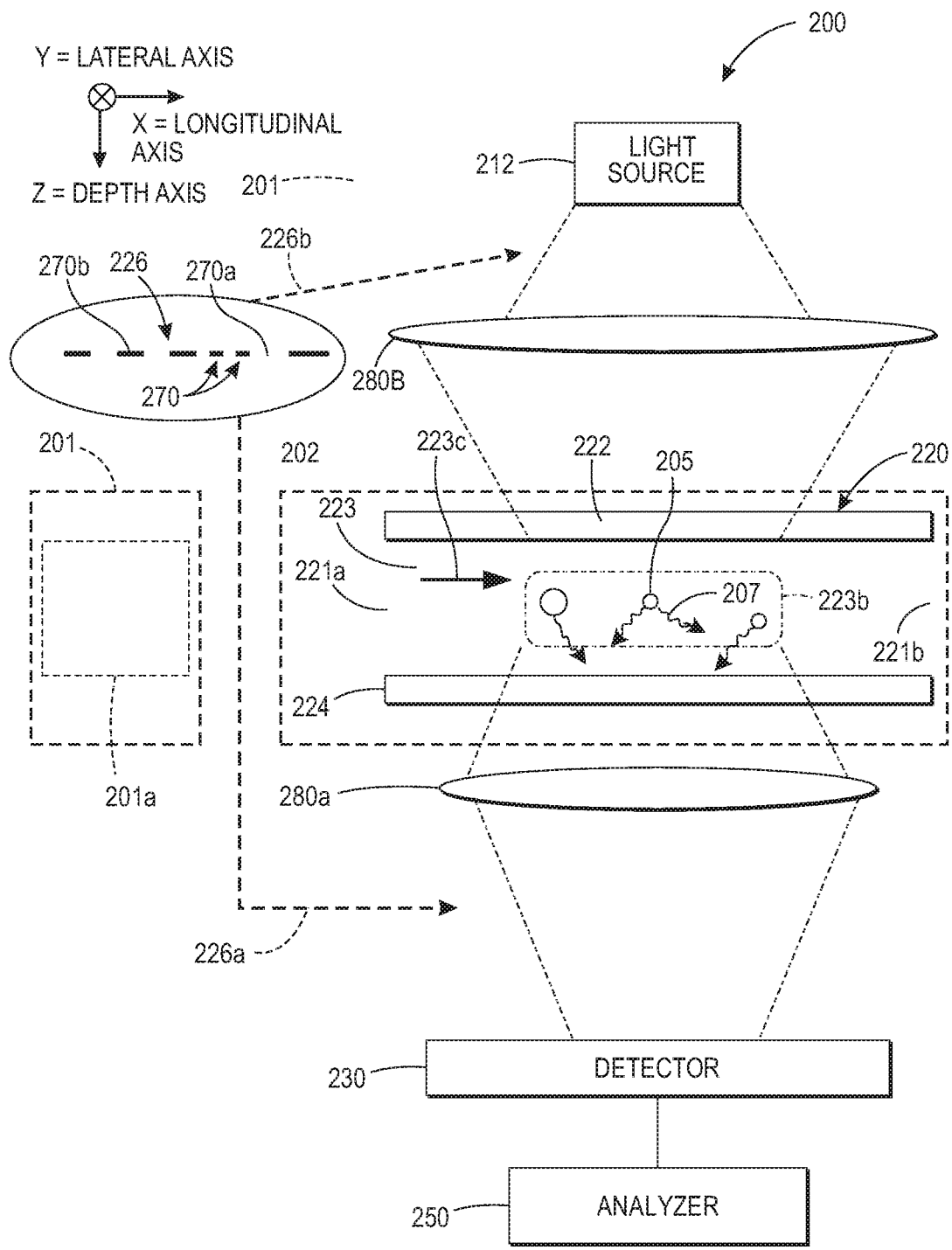
FIG. 2 is a schematic view of another example embodiment of an assembly with a delivery device containing a light source and an analyzer, and an injection portion containing a volume, an optical imaging element, and a detector.

FIG. 2 is an enlarged schematic view of a portion of an assembly 200 according to an example embodiment. The assembly 200 includes a delivery device 201 with an injector 201A, an intermediate portion 202, a volume 220, a detector 230, and a spatial filter 226. The delivery device 201 is configured to contain a particle 205 and the injector 201A accelerates the particle 205 in a desired direction (e.g., in an injection direction 223c) through a detection region 223b. In the embodiment shown in FIG. 2, the delivery device 201 can be hand held and a light source 212 and an analyzer 250 can be disposed external thereto. The intermediate portion 202 can be removably coupled to the delivery device 201 and can house the volume 220 through which the particles 205 pass. In the embodiment of FIG. 2, the detector 230, optics 280a such as a waveguide, lens, etc., and spatial filter 226 can be disposed external to the intermediate portion 202. Similarly, optics 280b can be used in some embodiments. As illustrated by arrows 226a and 226b, the spatial filter 226 can be disposed external to the delivery device 201 or the intermediate portion 202 in some instances. However, in other instances the spatial filter 226 can be housed within the intermediate portion 202 or the delivery device 201.

The volume 220 is adapted to receive an injected particle of interest to be analyzed. In particular, the volume can include a cavity, a void, a channel, and/or a pathway through which the particles 205 can pass. A sample containing one or more particles 205 may enter the volume 220 at an inlet 221a thereof and exit the volume 220 at an outlet 221b thereof, moving generally in the injection direction 223c through the volume 220 formed between confining members 222, 224. As illustrated in FIG. 2, the one or more particles 205 that comprise the sample can have differing sizes and differing depths within the volume 220 as measured in the z-direction of the Cartesian coordinate system illustrated. Each particle 205 may have a different position along the volume 220 in the x-direction (generally along the injection direction 223c of the volume 220) as well as different lateral position in the y axis direction of the Cartesian coordinate system within the volume 220.

As discussed previously, the spatial filter 226 may comprise, for example, a spatial mask. As will be discussed in greater detail subsequently, the spatial filter 226 may have a plurality of mask features 270. The mask features 270 include first features 270a having a first optical characteristic, e.g., more light transmissive regions, and second features 270b having a second optical characteristic, e.g., less light transmissive regions. For simplicity of explanation, many examples provided herein refer to mask features comprising more light transmissive regions and mask features or regions comprising less light transmissive regions. However, it will be appreciated that the optical characteristics of the first and second types of mask features may differ optically in any way, e.g., the first features may comprise regions having a first optical wavelength pass band and the second features may comprise regions having a second optical wavelength pass band different from the first optical wavelength pass band. The pattern or sequence of first features 270a and second features 270b define a transmission function that changes based on a three dimensional position of a light 207 emanating from the particle 205 within the volume 220 (i.e., as measured along the x-direction, y-direction, and z-direction of the Cartesian coordinate system). This transmission function may be substantially periodic, or it may instead be substantially non-periodic. The transmission function is sensed by the detector 230, which is configured to output the time-varying output signal discussed in FIG. 1 in response.

In the embodiment of FIG. 2, the spatial filter 226 may be substantially monochromatic or polychromatic as desired. In a monochromatic mask, the first features 270a may be more light transmissive and may all have substantially the same transmission characteristic, and the second features 270b may be less transmissive than the first features or may be non-transmissive (opaque) and also all have substantially the same transmission characteristic (different from that of the first features 270a). In a simple case, the transmissive first features 270a may all be completely clear, as in the case of an aperture, and the less transmissive second features 270b may be completely opaque, as in the case of a layer of black ink or other absorptive, reflective, or scattering material. Alternatively, the transmissive first features 270a may all have a given color or filter characteristic, e.g., high transmission for light emanating from an excited object, but low transmission for excitation light. Alternatively, the less transmissive second features 270b may have a low but non-zero light transmission, as in the case of a grey ink or coating, or a partial absorber or reflector.

Figure 3:
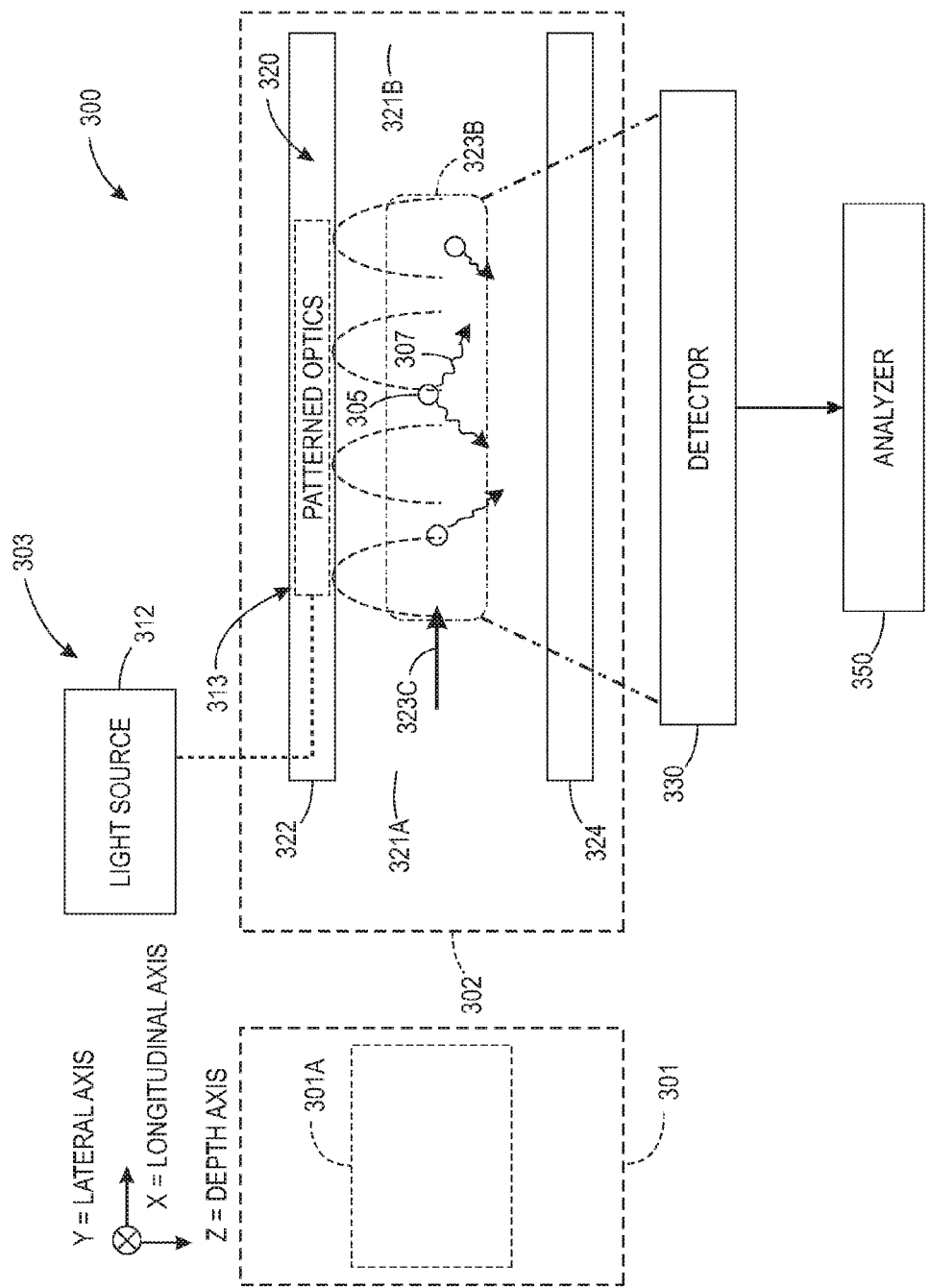
FIG. 3 is a schematic view of another example embodiment of an assembly using one or more optical components such as micro-optics.

FIG. 3 is a schematic view of another embodiment of a portion of an assembly 300. The portion of the assembly 300 illustrated includes a delivery device 301, an intermediate portion 302, optical components 303, a volume 320, a detector 330, and an analyzer 350. The delivery device 301 is configured to contain a particle 305 and has an injector 301A adapted to accelerate the particle 305 in a desired direction (e.g., in an injection direction 323c). In the embodiment shown in FIG. 3, the delivery device 301 can be hand held and has the optical components 303 such as a light source 312 and the analyzer 350 disposed external thereto. The intermediate portion 302 can be removably coupled to the delivery device 201 and can house the volume 320, and in some instances portions of the optical components 303 such as light directing components 313.

In the embodiment of FIG. 3, the light source 312 is configured to provide a measurement light that is used to illuminate the particle 305. In some cases, the light source 312 can comprise optical components such as micro-optics or a patterned light source configured to create a patterned measurement light in the detection region 323b. In other embodiments, the measurement light can be patterned by the spatial arrangement of the light directing components 313. The light directing components 313 are in optical communication with the light source 312 and receive the measurement light. As illustrated in FIG. 3, in some instances the light directing components 313 can extend through at least a part of the intermediate portion 302 such as a confining member 322 of the volume 320. The measurement light can be imaged and/or directed onto the detection region 323b by the light directing components 313. The light directing components 313 can include components for imaging light (e.g., lenses) and/or components for directing light, (e.g., fiber optics or waveguides).

Similar to the embodiments of FIGS. 1 and 2, the volume 320 includes an inlet 321a and an outlet 321b, for one or more particles 305 traveling in an injection direction 323c. In some instances such as in FIG. 2, the volume 320 may be bounded by one or more confining members 322, 324.

In FIG. 3, the light directing components 313 are spaced in a known spaced relationship from one another. Thus, the measurement light emitted into the volume 220 is in a known spatial relationship. In response to the measurement light, the light emanating 307 from the particles 305 experiences a modulation in intensity and other characteristics due to variation in the intensity and other characteristics of the measurement light. The modulation in intensity and other characteristics of the light emanating 307 from the particle 305 is captured by the detector 330. The pattern or sequence of light emanating 307 define a transmission function that changes based on a three dimensional position of the light 307 emanating from the particle 305 within the volume 320 (i.e., as measured along the x-direction, y-direction, and z-direction of the Cartesian coordinate system). This transmission function may be substantially periodic, or it may instead be substantially non-periodic. The transmission function is sensed by the detector 330, which is configured to output the time-varying output signal discussed in FIG. 1 in response.

Figure 4:
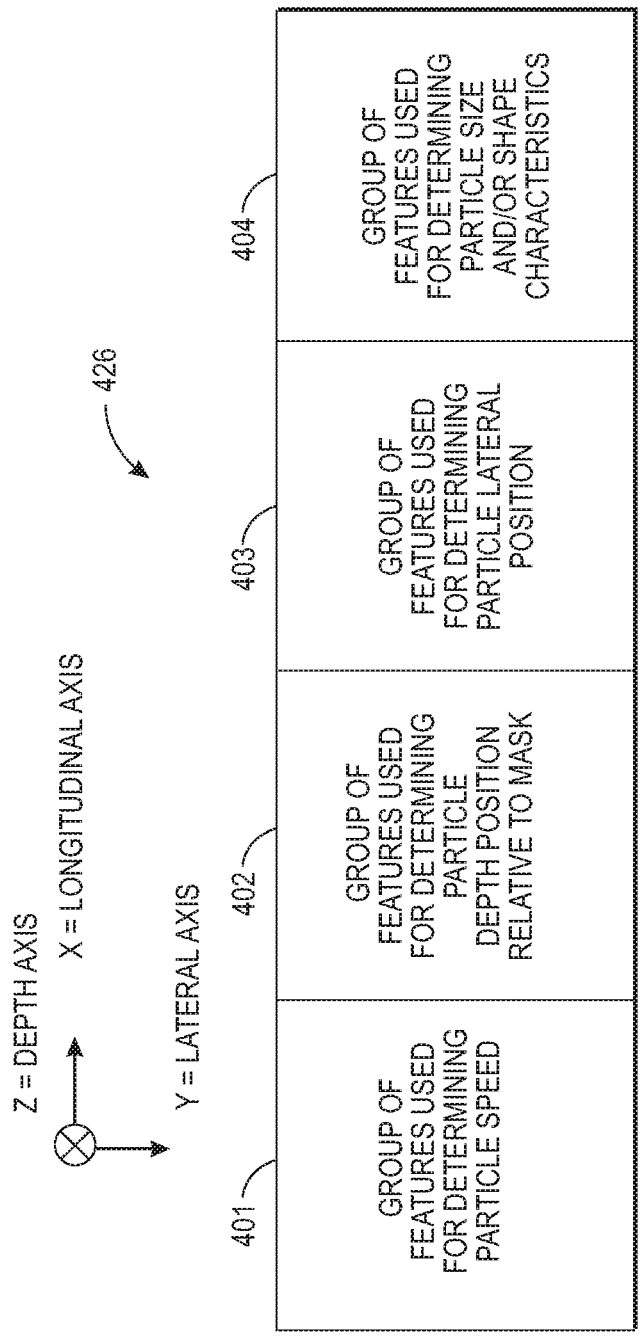
FIG. 4 is a highly schematic arrangement of one or more spatial filters having groups of features for determining various characteristics of a particle according to an exemplary embodiment.

FIG. 4 illustrates a highly schematic arrangement for a spatial filter 426. The spatial filter 426 can include multiple types of mask features that may be used to determine the characteristics of a particle during a delivery and/or a reflected path. Although illustrated as grouped separately along the longitudinal axis in FIG. 4, it should be recognized regions 401, 402, 403, and 404 can be interdisposed with one another and/or can be grouped adjacent one another along the lateral and/or depth axes. FIG. 4 illustrates a spatial filter 426 that includes first, second, third, and fourth regions 401, 402, 403, and 404, wherein a first group of features useful for determining a speed of the particle (either along the delivery or the reflected path) are disposed within the first region 401, a second group of features useful for determining a depth position of the particle within the volume (either along the delivery or the reflected path) are disposed within the second region 402, a third group of features useful for determining lateral position within the volume (either along the delivery or the reflected path) are disposed within the third region 403, and a fourth group of features useful for determining a size and/or shape of the particle (either along the delivery or the reflected path) are disposed within the fourth region 404. As discussed, in some instances the spatial filter can include less or more than four regions. Additionally, different groups of features may be disposed within the same region (interdisposed). For example, the first group of features used to determine the speed may be disposed in regions 403 and/or 404 and the second group of features used to determine depth position can be disposed in regions 401, 403, and/or 404. The longitudinal arrangement of the different groups of features may be changed from embodiment to embodiment and some regions may be used in along the depth axis or lateral axis rather than being disposed along the longitudinal axis as illustrated. Not all regions may be used in some embodiments of the spatial filter.

Figure 5A:
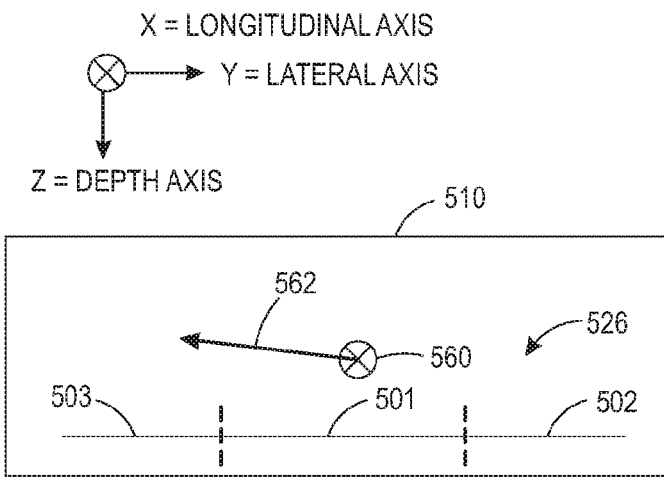
FIGS. 5A and 5B illustrate an arrangement of spatial filters that are used to determine particle characteristics along a delivery path, and if necessary, along a reflected path.
Figure 5B:
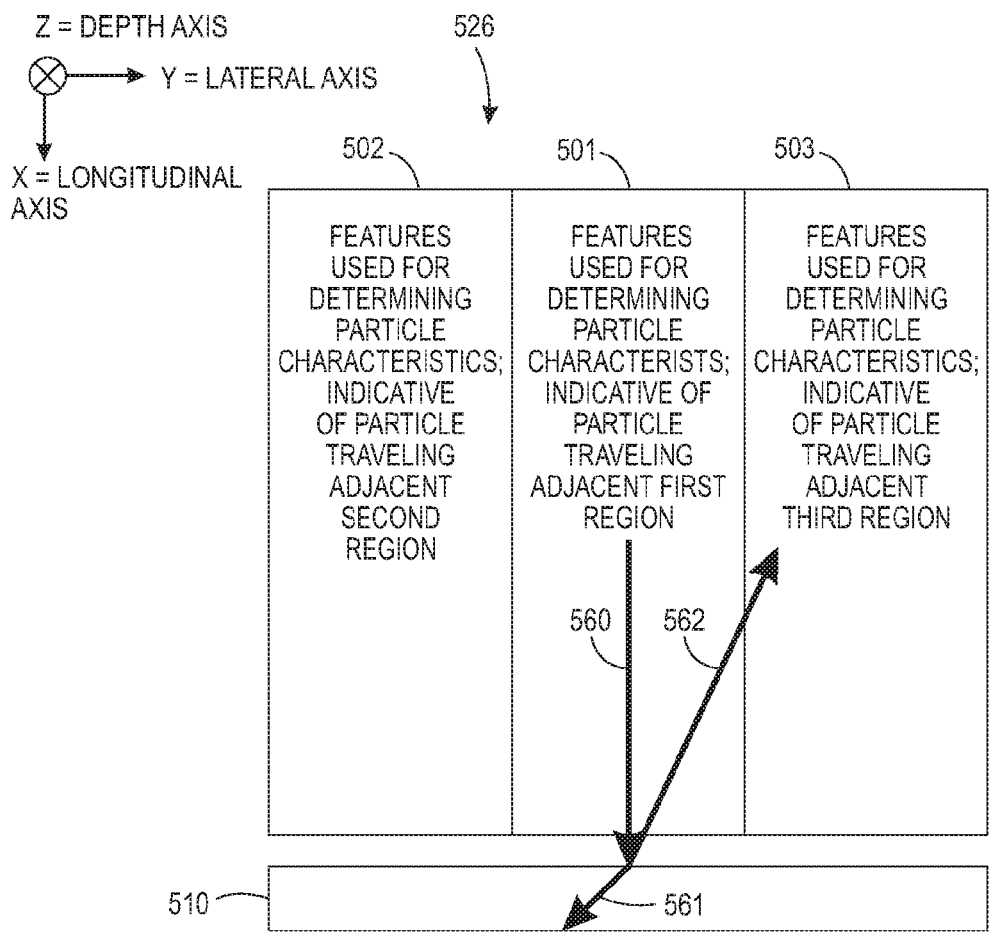

FIGS. 5A and 5B illustrate a highly schematic arrangement of a spatial filter 526 and a biological tissue 510. As illustrated, the spatial filter 526 can be arranged adjacent the biological tissue 510. FIGS. 5A and 5B illustrate the spatial filter 526 extending in three dimensions along the x-y plane. In other embodiments, the spatial filter 526 can be disposed to extend in varies additional planes relative to the longitudinal, lateral, and depth axes. The spatial filter 526 can include one or more regions having the same ore different features. The spatial filter 526 has been illustrated with three regions of features 501, 502, and 503. In FIGS. 5A and 5B, the region of features 501, 502, and 503 are arranged substantially in the x-y plane. In other embodiments, the first, second, and third regions 501, 502, and 503 are arranged as extending in the x, y, and z directions. For example, in some instances the second and third regions 502 and 503 can be arranged at substantially 90° to the first region 501. However, in other embodiments the second and/or third regions 502 and 503, if either is used, can be arranged at any angle relative to the first region 501.

In the embodiment shown in FIG. 5B, the first region 501 can have features that are used for determining particle characteristics when the particle travels adjacent the first region 501. Thus, a signal generated corresponding to the first region 501 is indicative of the particle traveling adjacent the first region 501. Similarly, the second region 502 can have features that are used for determining particle characteristics when the particle travels adjacent the second region 502. A signal generated corresponding to the second region 502 is indicative of the particle traveling adjacent the second region 502. In some instances, the second region 502 is given features that differ from the first region 501 (as illustrated in FIG. 5B) such that the signal generated by the particle would change once the particle moves along a trajectory that takes the particle from adjacent the first region 501 to adjacent the second region 502.

The third region 503 can have features that are used for determining particle characteristics when the particle travels adjacent the third region 503. A signal generated corresponding to the third region 503 is indicative of the particle traveling adjacent the third region 503. In some instances, the third region 503 is given features that differ from the first region 501 (as illustrated in FIG. 5B) such that the signal generated by the particle would change once the particle moves along a trajectory that takes the particle from adjacent the first region 501 to adjacent the third region 503.

In some instances, the first region 501 is used primarily to aid in the determination of one or more characteristics of the particle along the delivery path and the second and third regions 502 and 503 may have features that can be used primarily to aid in the determination of one or more characteristics of the particle along a reflected path. In other embodiments, the regions 501, 502, and 503 can be used to aid in the determination of characteristics of the delivery path and the reflected path equally or in another fashion not specifically described in reference to the embodiment of FIG. 5B.

FIGS. 5A and 5B illustrate the delivery path 560, an injected path 561 (shown in FIG. 5B only), and the reflected path 562 with arrows. The delivery path 560 extends along the spatial filter 526 to the biological tissue 510. Once a particle traveling along the delivery path 560 contacts the biological tissue 510 the particle can travel on one of the injected path 561 and the reflected path 562. If delivery of the particle is successful, the particle will enter the biological tissue 510 along the injected path 561. However, if delivery of the particle is unsuccessful, the particle will travel back along the reflected path 562 relative to the spatial filter 526.

It should be noted that successful delivery of the particle along the injected path 561 into the biological tissue will not be detected, and a time-varying signal will not be generated. Only modulated light from the delivery path 560 and the reflected path 562 can be detected. As discussed previously, in addition to being able to aid in the determination of one or more characteristics of the particle along the delivery path 560 and/or one or more characteristics of the particle along the reflected path 562, the spatial filter 526 can aid in determining the success of particle injection into the biological tissue 510. This determination of success can be accomplished by an analyzer appropriately configured to distinguish between the delivery path 560 and the reflected path 562 for each particle passing adjacent the spatial filter 526.

Figure 6A:
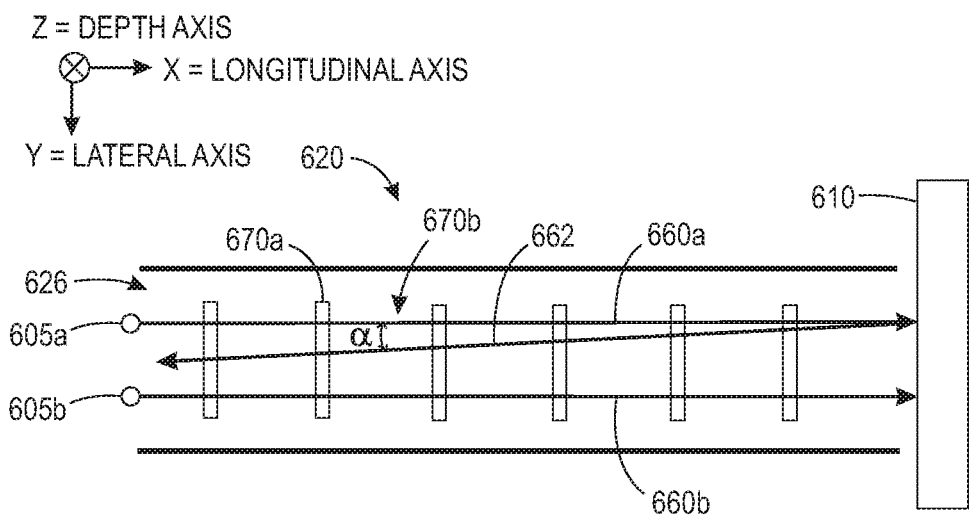
FIG. 6A is a plan view of a volume and spatial filter disposed adjacent a biological tissue and illustrating delivery paths and a reflected path for two particles.

FIG. 6A illustrates an arrangement of a spatial filter 626 adjacent a volume 620. The volume 620 extends to adjacent a biological tissue 610. A first particle 605a and a second particle 605b are disposed within the volume and are each illustrated as having a delivery path 660a and 660b to the biological tissue 610. The second particle 605b is injected into the biological tissue 610 while the first particle 605a is redirected along a reflected path 662. As shown in FIG. 6A, the particles may be disposed in different lateral positions within the volume 620. The reflected path 622 can have a different trajectory than the delivery path 660a and can vary not only by the angle α illustrated in the lateral direction but also by angles with respect to the depth axis and longitudinal axis. The trajectory and angles of the reflected path 662 and the delivery path 660a can be determined with the aid of the spatial filter 626. The reflected path 662 can have a speed and a lateral trajectory angle with respect to the biological tissue 610 within the volume 620 that can be determined with the aid of the spatial filter 626. The incoming and reflected particle can have a different speed and/or size/shape, for example, in the case where the particle experienced energy loss at the tissue interface and/or part of the particle entered the biological tissue 610 and another part of the particle was scattered back from the surface along the reflected path 662. Since the tissue surface can be relatively rough, backscattering can occur in many different directions rather than a single direction as illustrated.

Figure 6B:
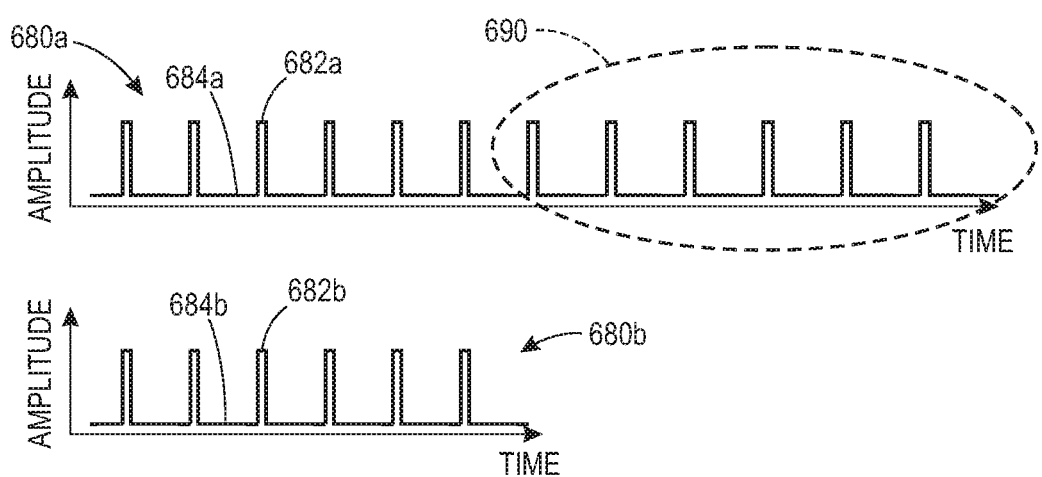
FIG. 6B is a plot of time-varying signals generated from the two particles of FIG. 6A.

FIG. 6B illustrates two time-varying signals 680a and 680b generated by the movement of the particles 605a and 605b through the volume 620. In particular, the movement of the particles 605a and 605b past more transmissive features 670a leads to regions 682a and 682b of the first time-varying signal 680a and the second time-varying signal 680b that have higher amplitude relative to regions 684a and 684b. Regions 684a and 684b result from the particles 605a and 605b passing adjacent less transmissive features 670b that block or at least partially block light emissions from the particles 605a and 605b.

As illustrated in FIG. 6B, light emanating from the first particle 605a is detected and the first time-varying signal 680a generated. Similarly, light emanating from the second particle 605b is detected and the second time-varying signal 680b generated. The first time-varying signal 680a is generated from light captured on both the delivery path 660a and the reflected path 662. In contrast, the second time-varying signal 680b has a shorter duration than the first time-varying signal 680a and is generated from light captured only on the delivery path 660b as the particle 605b is successfully delivered.

The difference in the duration between the first time-varying signal 680a and the second time-varying signal 680b can be one factor in determining if the particle has been successfully delivered to the biological tissue 610. Additionally, as shown in FIG. 6B, the first time-varying signal 680a may have one or more characteristics (amplitude, frequency, pitch, etc.) that aid in determination of one or more characteristics of the particle 605a along the delivery path 660a as well as one or more characteristics of the particle 605a along the reflected path 662. For example, reviewing the first time-varying signal 680a one may ascertain the speed of the particle 605a and determine that the speed of the particle 605a during the delivery path 660a differs from the speed of the particle during the reflected path 662 as indicated by the change in the first time-varying signal 680a that occurs in region 690.

Figure 7:
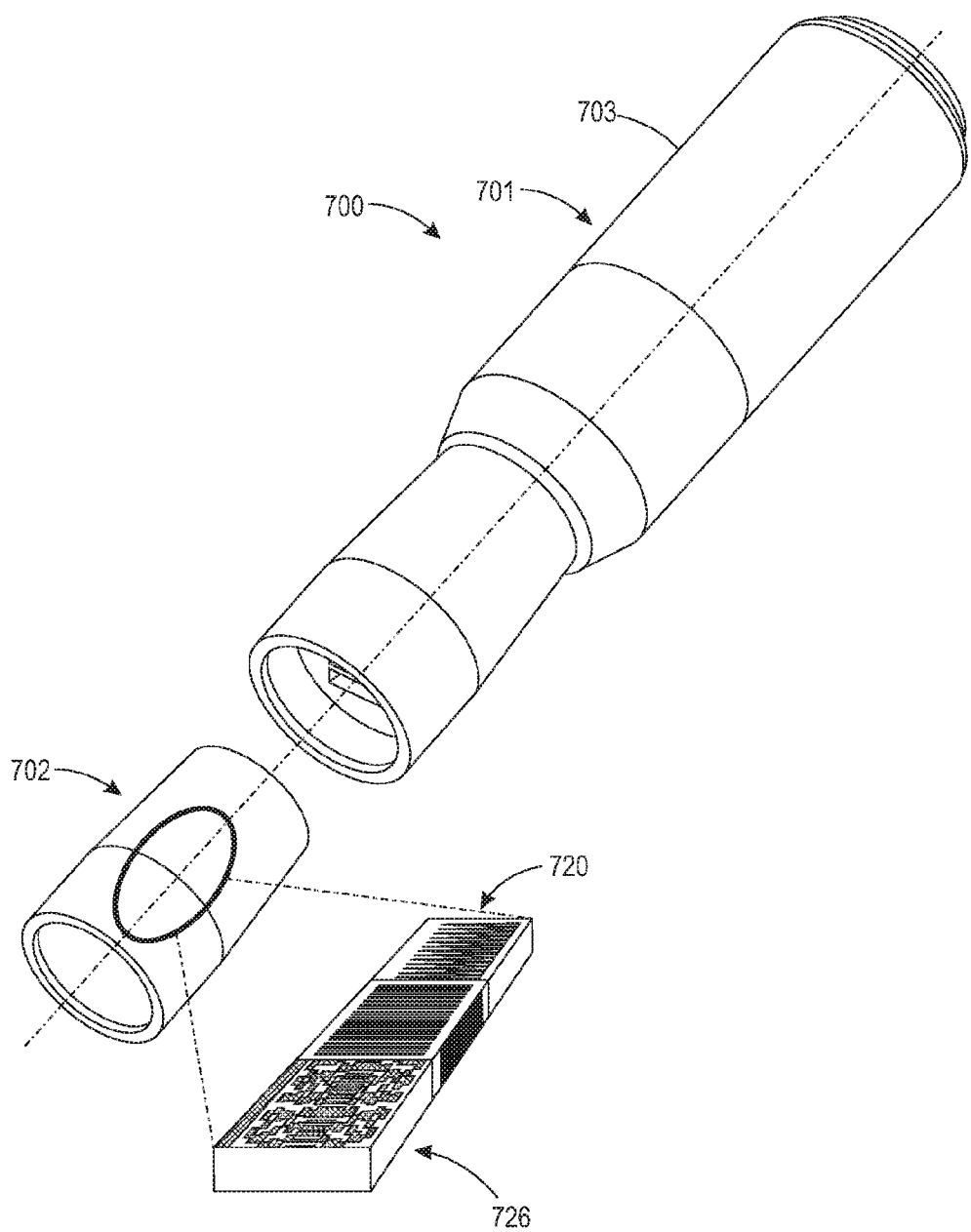
FIG. 7 is a perspective view of a drug delivery device and an injection portion according to one example embodiment.

FIG. 7 is a perspective view of an assembly 700 of a delivery device 701 and an intermediate portion 702. The delivery device 701 includes a hand held housing 703 and the intermediate portion 702 is adapted to be removably coupled to the hand held housing 703. The delivery device 701 is adapted to accelerate one or more particles. In some embodiments, such as an embodiment that utilizes a drug delivery apparatus as disclosed in Uhland et al., the delivery device can be configured to entrain a particle with a pressurized gas, and direct a collimated stream comprised of the particle and the pressurized gas in a desired direction. The delivery device 701 and an analyzer (FIG. 3) can be disposed within the hand held housing 703 in some instances.

In addition to coupling to the delivery device 701, the intermediate portion 702 is adapted to be applied to a surface of a biological tissue. As previously discussed, the intermediate portion 702 can contain a portion of the optical component (FIG. 3) and a detector (FIG. 3). In some instances, the intermediate portion 702 can include at least one transparent wall that allows for the passage of one or more of a measurement light and a light emanating from the particle to pass therethrough. Additionally, the embodiment of FIG. 7 illustrates that a volume 720 and spatial filters 726 can be disposed within the intermediate portion 702.

Figure 8:
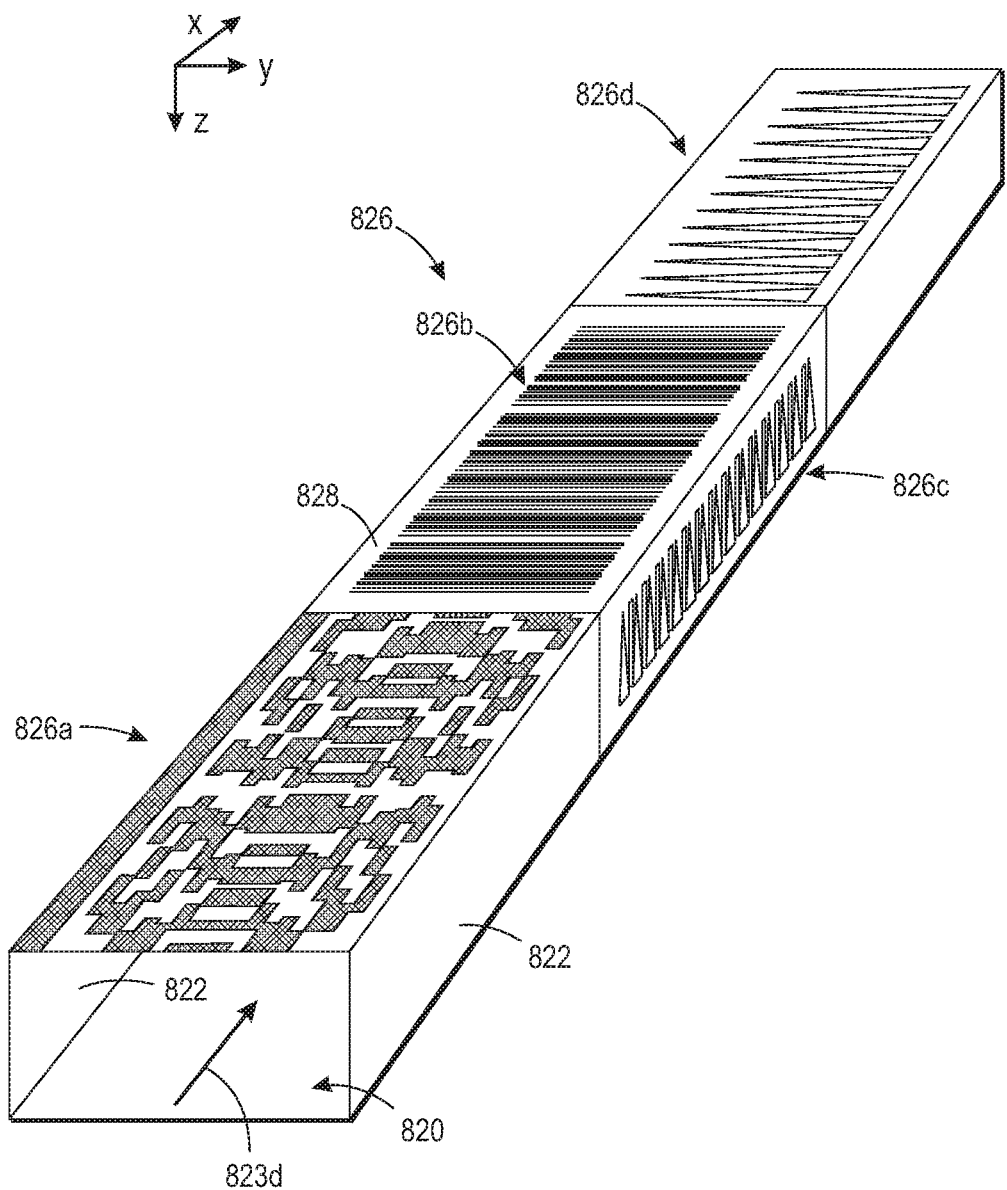
FIG. 8 is a perspective view of a portion of a volume having four spatial filters arranged adjacent thereto according to an example embodiment.

FIG. 8 is an enlarged perspective view of spatial filters 826 and volume 820 according to an exemplary embodiment. The volume 820 includes a passageway through which an injection direction 823c is illustrated. The volume 820 can include confining members 822, 824, and 828. In other embodiments one or all of the confining members 822, 824, and 828 may not be used. The injection direction 623c aligns generally with the x-direction (longitudinal axis) of the Cartesian coordinate system illustrated in FIG. 6A. In the embodiment shown, the spatial filters 826 are comprised of several spatial filters 826a, 826b, 826c, and 826d. In some cases, the spatial filters 826a, 826b, 826c, and 826d can be disposed on the confining member 822, 824, and 828 for direct sensing. In other embodiments, the spatial filters 826a, 826b, 826c, and 826d may be disposed within the volume 820 and/or disposed at a distance from the confining members 822, 824, and 828 (remote sensing). Detectors (not shown) may be positioned in any appropriate location to sense modulated light passing through the spatial filters 826a, 826b, 826c, and 826d. As discussed previously, all the spatial filers 826a, 826b, 826c, and 826d illustrated may not be utilized in some embodiments. In yet other embodiments, additional spatial filters (not shown) can be used with the spatial filters 826 to determine additional characteristics of the particle along the delivery path and/or the reflected path. In yet other embodiments, the spatial filters 826a, 826b, 826c, and 826d can be disposed different angles relative one another rather than being disposed at the transverse angles as shown.

In FIG. 8, the spatial filter 826a is arranged in the x-y plane of the Cartesian coordinate system. The spatial filter 826a has a plurality of mask features arranged in a pattern that is useful in determining a size and/or shape of the particle. The spatial filter 826b has a plurality of mask features arranged in a pattern that is useful in determining one or both of the depth of the particle within the volume (i.e., a depth in the z-axis direction) and a length of the particle in the longitudinal direction (i.e., in the x-axis direction). Further discussion of this spatial filters 826a and 826b and mask features can be found subsequently and in the Applicant's previously discussed co-pending applications.

Spatial filter 826c is arranged in the x-z plane while spatial filter 826d is arranged in the x-y plane of the Cartesian coordinate system. Spatial filters 826c and 826d have a plurality of mask features arranged in a pattern that is useful in determining the trajectory, lateral position (i.e., a position in the y-direction of the Cartesian coordinate system), depth (i.e., a position in the z-direction of the Cartesian coordinate system) of a particle within the volume 820) of a particle within the volume 820 as further discussed in Applicant's co-pending applications.

Multiple detectors (not shown) may be positioned in any appropriate locations to sense modulated light passing through the filters. The spatial filters 826c and 826d are useful for determining lateral position and/or depth position of particles due to triangular features. It will be appreciated features other than triangular features can be used in various embodiments. Using spatial filters to modulate light as described herein, the position of a particle in the volume can be determined using a spatial filter that has mask features with a changing characteristic such as an edge between first and second mask features having a non-perpendicular and non-parallel orientation with respect to an injection direction along the volume. The changing characteristic causes a change in at least one of the duty cycle, frequency, or phase in the time-varying signal generated by the detector. In many applications it may be useful to determine the speed of the particles. Particle speed can be determined by determining the frequency of the transitions in the time-varying output signal and/or by transforming the time-varying signal to a frequency domain signal and analyzing the dominant frequencies having the largest amplitude.

It should be appreciated that the system of FIG. 8 is capable of determining the position of a particle in three dimensions using spatial filters 826. As such, the disclosed embodiment uses two (or more) masks oriented in different planes. For example, the fourth spatial filter 826d includes a first group of mask features that can be used for detecting lateral position and the second and third spatial filters 826b and 826c include groups of mask features may be used for detecting a depth position as well as a trajectory along the depth axis. A first detector can be arranged relative to the fourth spatial filter 826d (and in some instances the first and second spatial filters 826a and 826b) so that the first detector detects light emanating from particles flowing along the volume 820 that is spatially modulated by the fourth spatial filter 826d (and in some instances the first and second spatial filter 826a and 826b). The first detector generates a first time-varying signal in response to the emanating light that is spatially modulated by the fourth spatial filter 826d. A second detector is oriented relative to the third spatial filter 826c so that the second detector detects light emanating from particles flowing along the volume 820 that are spatially modulated by the third spatial filter 826c. In FIG. 8, a relatively complex spatial filter arrangement with complex mask patterns is shown in order to illustrate the full potential of the disclosed techniques, however, in many cases a relatively simple periodic mask which is useful in determining speed (from frequency of the time modulated signal) and/or size (from the shape of the time-modulated signal) for incoming and/or reflected particles is sufficient to allow for analysis of the injector system to determine if the injector parameter is sufficient or modification is desirable.

Figure 9A:
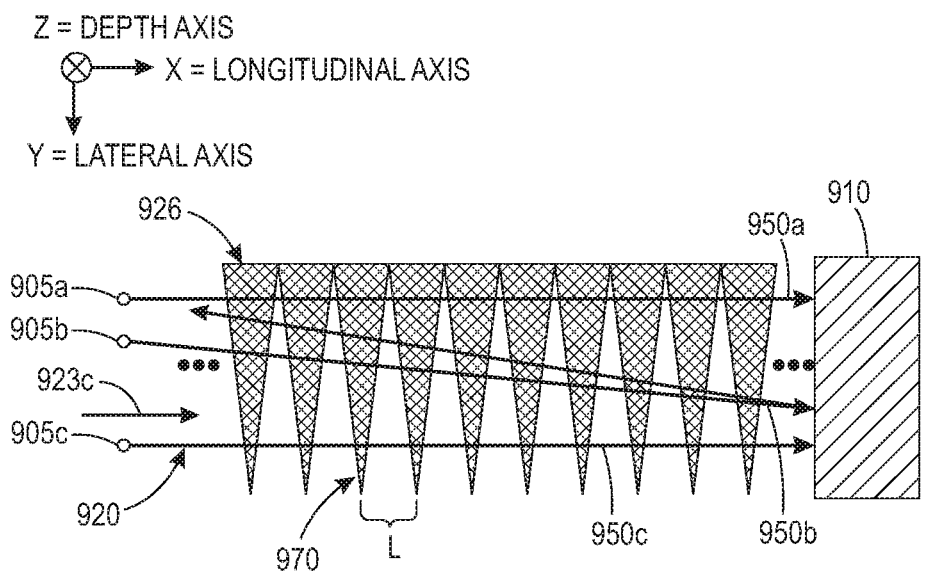
FIG. 9A is a plan view of particles moving relative to a spatial filter along a delivery paths and a reflected path according to another embodiment.

FIG. 9A shows a top plan view of another embodiment of a spatial filter 926 disposed adjacent a biological tissue 910. The spatial filter 926 has mask features 970 that each have a length L with respect to a longitudinal direction (as measured relative to the x axis) of the volume 920 that changes as each feature 970 extends across a width of the volume 920 as measured relative to the y axis. The mask features 970 include transmissive and less transmissive regions and edges of some transmissive regions extend at a non-perpendicular angle with respect to an injection direction 923c along the volume 920. As shown in FIG. 9A, the mask features 970 are periodic with respect to the injection direction 923c and a duty cycle of the mask features 970 changes along the lateral width of the volume 920. Although embodiments illustrated herein show triangular mask features 970, the mask features could alternatively be truncated triangles, interdigitated triangles, parallelograms, or any other shape that has an edge that varies non-perpendicularly with respect to the injection direction 923c. FIG. 9A additionally shows particles 905a, 905b, and 905c with different trajectories through the volume 920 during delivery paths 950a, 952b, and 952c. Particle 905b is not successfully delivered into the biological tissue 910, and therefore, includes a reflected path extending back through the volume 920.

Figure 9B:
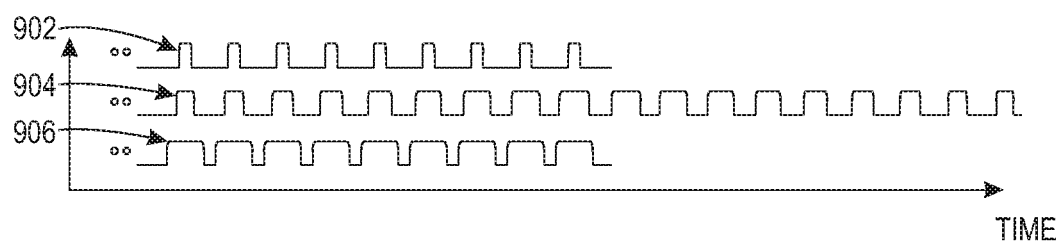
FIG. 9B is a plot that shows time-varying signals that result from the three delivery paths and one reflected path illustrated in FIG. 9A.

FIG. 9B is a plot that shows time-varying signals 902, 904, and 906 that result from the particles 905a, 905b, and 905c flowing through the volume relative to the spatial filter 926 along delivery paths 950a, 950b, and 950c. The time-varying signal 902 corresponds with the delivery path 950a of particle 905a, the time-varying signal 904 corresponds with the delivery path 950b and the reflected path of particle 905b, and the time-varying signal 906 corresponds with the delivery path 950c of the particle 905c. The time-varying signal 904 also extends to the reflected path of the particle 905b as indicated by the longer duration of that time-varying signal 904 relative to the time-varying signals 902 and 906.

As shown in the plot of FIG. 9B, the characteristics of the time-varying signals 902, 904, and 906 are correlated to the geometry of the mask features 970 and correspond to the lateral location of the particles 905a, 905b, and 905c within the volume 920 relative to the spatial filter 926. Thus, the time-varying signal 902 has a relatively small duration of non-zero amplitude due to the small length L of the transmissive features 970 along delivery path 950a. The configuration of the spatial filter 926 also allows for determination of the trajectory of the particles 905a, 905b, and 905c in the x-y plane based upon changes in the characteristics of the signals. For example, time-varying signal 904 has an increased duration of the signal in a peak region as the particle 905b flows along the filter 926 in the x and y directions during the delivery path and experiences has an decreased duration of the signal in a peak region as the particle 905b flows along the filter 926 in the x and y directions during the reflected path. The change in duration of the peak region results from changes in the length L (in the x direction) of the transmissive features 970.

As discussed previously, a determination of delivery success of each particle 905a, 905b, and 905c into a biological tissue 910 based upon characteristics of the corresponding time-varying signal can be conducted by an analyzer. In the embodiment shown in FIG. 9B, the characteristics of interest to delivery success can include the relative duration of the time-varying signals. For example, time-varying signal 904 has a longer relative duration than time-varying signals 902 and 906 indicating a likelihood of a delivery failure rather than a successful delivery. As is further discussed in the Applicants' co-filed applications, in particular, application Ser. No. 14/181,560, entitled "Spatial Modulation of Light to Determine Object Position", application Ser. No. 14/181,524, entitled "Spatial Modulation of Light to Determine Dimensional Characteristics of Objects in an Injection Direction" and application Ser. No. 14/181,530, entitled "Spatial Modulation of Light to Determine Object Length" a speed difference of incoming and/or reflected signal as well as shape difference (indicative for particle size) of incoming and/or reflected signal can provide information on delivery success and/or how to adjust one or more characteristics of the delivery of the particle (also referred to as an injection parameter) such as e.g., a speed of the particle during the delivery path, a size of the particle in one or more of three dimensions, and a three dimensional position of the particle within the volume during the delivery path.

Figure 10:
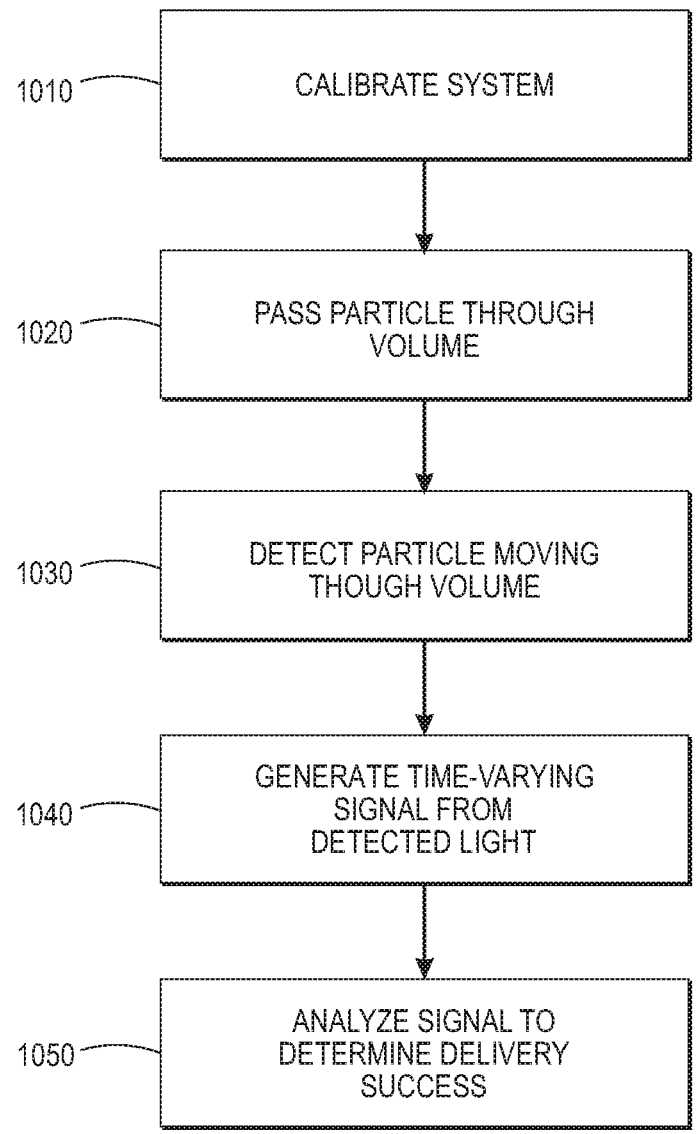
FIG. 10 is a flow diagram of a method for monitoring delivery of particles to biological tissue.

FIG. 10 shows a flow diagram of a method of monitoring delivery of one or more particles according to one embodiment. As part of an optional initialization 1010 for the system, particles of a known size and/or luminescence are passed through a volume relative to a spatial filter at different depths and/or lateral positions so that the system can be calibrated. The volume is placed adjacent a biological tissue and one or more particles of interest are passed through the volume in step 1020. A light from the particle is detected 1030 as the particle moves through the volume relative to the spatial filter. As discussed previously, the detected light can be modulated according to mask features of the spatial filter. A time-varying signal is generated 1040 in response to the detected light. The signal is analyzed 1050 to determine a delivery success of the particle into the biological tissue based upon characteristics of the time-varying signal.

Figure 11:
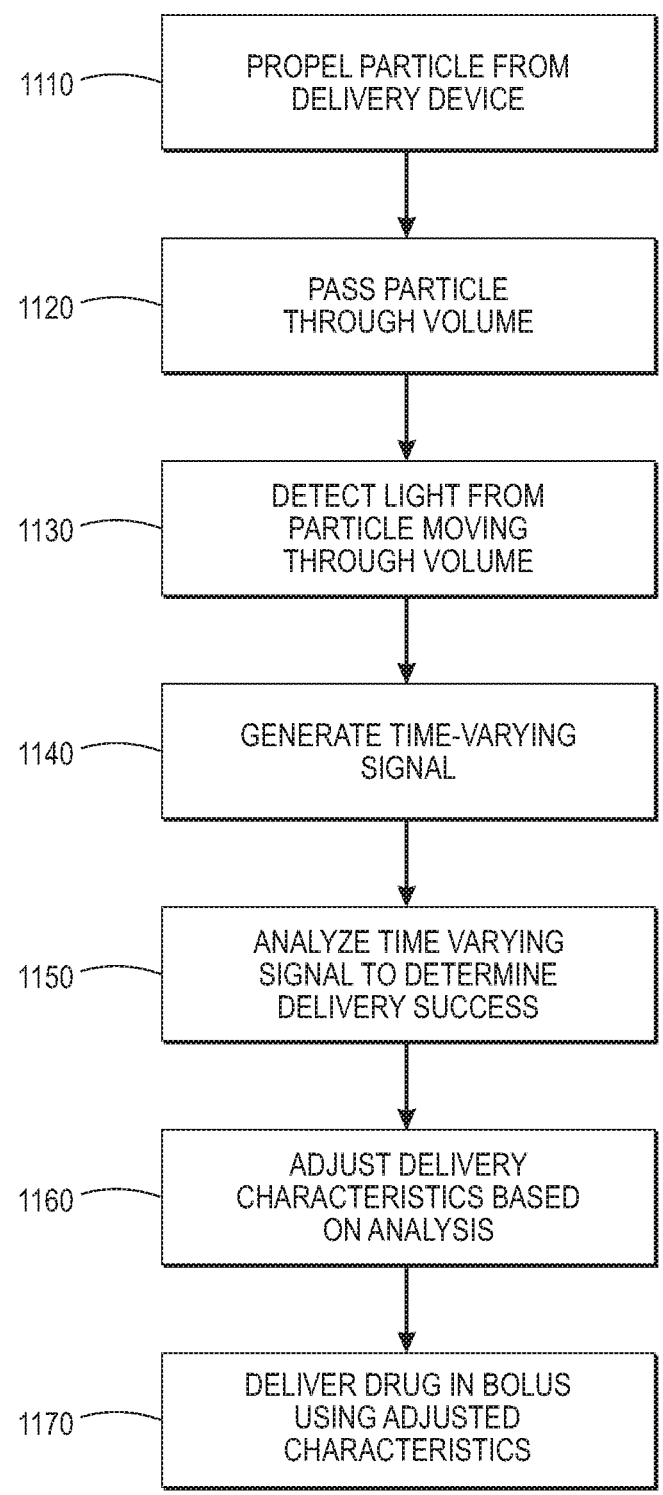
FIG. 11 is a flow diagram of transcutaneous drug delivery according to one embodiment.

FIG. 11 shows a flow diagram of a method of transcutaneous drug delivery according to one embodiment. The method propels particles individually or a few at a time from a delivery device in step 1110. The particles are passed through a volume 1120 and a light from the particles is detected moving through the volume 1130. A time-varying signal is generated in response to the detected light 1140 and the time-varying signal is analyzed to determine a delivery success of the particles at penetration into the biological tissue 1150. The delivery characteristics of the particles can be iteratively adjusted based on the analysis until a predetermined success rate is achieved 1160. The drug can be delivered in a bolus of many particles using the adjusted delivery characteristics 1170 in some instances.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. An assembly for delivering and monitoring delivery of particles to a material, comprising:
   a delivery device configured to contain a particle and accelerate the particle in a desired direction and across an interface into the material;
   a volume through which the particle can pass;
   a spatial filter having mask features;
   a detector positioned to detect light emanating from the particle along a detection region within the volume, the detected light is modulated according to the mask features as the particle moves along the detection region, the detector configured to generate a time-varying signal in response to the detected light; and
   an analyzer configured to receive the time-varying signal and determine a delivery success of the particle into the material based upon characteristics of the time-varying signal.

2. The assembly of claim 1, wherein the volume has the material disposed adjacent thereto, and wherein the delivery success is measured by distinguishing between one or more of a delivery path and a reflected path of the particle through the material.

3. The assembly of claim 2, wherein the analyzer is configured to analyze one or more properties of the material.

4. The assembly of claim 3, further comprising control circuitry configured to vary one or more characteristics of delivery of the particle based upon one or more of analyzed properties of the material and one or more characteristics of the reflected path.

5. The assembly of claim 4, wherein the one or more characteristics of the delivery of the particle comprise a speed of the particle during the delivery path, a size of the particle in one or more of three dimensions, and a three dimensional position of the particle within the volume during the delivery path.

6. The assembly of claim 4, wherein the one or more characteristics of the reflected path comprise a speed of the particle during the reflected path and three dimensional position of the particle within the volume during the reflected path.

7. The assembly of claim 1, wherein the volume is housed within a disposable intermediate portion that reversibly engages with the delivery device.

8. The assembly of claim 7, wherein the material comprises a biological tissue, and wherein the intermediate portion is adapted to contact the biological tissue.

9. The assembly of claim 7, wherein the intermediate portion includes at least one transparent wall that allows for passage of one or more of a measurement light and the light emanating from the particle to pass therethrough.

10. The assembly of claim 9, further comprising at least one optical component configured to provide the measurement light, wherein the optical component includes one or more light directing components that can direct the measurement light.

11. The assembly of claim 10, wherein one or more of the spatial filter and the one or more light directing components are formed in the intermediate portion.

12. The assembly of claim 1, wherein the delivery device includes an injector is configured to entrain the particle with a pressurized gas, and direct a collimated stream comprised of the particle and the pressurized gas in the desired direction.

13. A system for monitoring delivery of particles to biological tissue, comprising:
a volume through which a particle can pass in a desired direction;
an optical component configured to provide a measurement light;
a detector positioned to detect light emanating from the particle in response to the measurement light, the detected light being modulated as the particle moves along a detection region within the volume, the detector configured to generate a time-varying signal in response to the detected light; and
an analyzer configured to receive the time-varying signal and determine a delivery success of the particle into the biological tissue based upon characteristics of the time-varying signal.

14. The system of claim 13, further comprising:
a delivery device including a hand held housing, wherein the delivery device is adapted to accelerate the particle toward the biological tissue; and
an intermediate portion removably coupled to the hand held housing, wherein at least the volume is disposed in the intermediate portion.

15. The system of claim 14, wherein the intermediate portion is adapted to be applied to a surface of the biological tissue.

16. The system of claim 13, further comprising a delivery device configured to entrain the particle with a pressurized gas, and direct a collimated stream comprised of the particle and the pressurized gas in the desired direction through the volume.

17. The system of claim 13, further comprising a spatial filter having mask features, wherein the detected light is modulated according to the mask features as the particle moves along the detection axis.

18. The system of claim 13, wherein the optical component is configured to create a patterned excitation in the particle along the detection region.

19. A method of monitoring delivery particles to biological tissue, comprising:
passing a particle through a volume that includes the biological tissue disposed adjacent thereto;
detecting a light from the particle moving through the volume relative to a spatial filter;
generating a time-varying signal in response to the detected light; and
analyzing the time-varying signal to determine a delivery success of the particle into the biological tissue based upon characteristics of the time-varying signal.

20. The method of claim 19, wherein the detected light is modulated according to mask features of the spatial filter.

21. The method of claim 19, wherein the step of analyzing determines properties of the biological tissue.

22. The method of claim 21, further comprising varying one or more characteristics of particle delivery based upon analyzed properties of one or more of the biological tissue and delivery characteristics of a reflected path.

23. The method of claim 19, further comprising distinguishing between one or more of a delivery path, and a reflected path of the particle through the volume to determine the delivery success of the particle into the biological tissue.

24. The method of claim 19, further comprising illuminating the particle with a patterned excitation light.

25. A method of transcutaneous delivery of a drug, comprising:
propelling particles individually or a few at a time from a delivery device;
passing the particles through a volume;
detecting a light from the particles moving through the volume;
generating a time-varying signal in response to the detected light;
analyzing the time-varying signal to determine a delivery success of the particles at penetration into a biological tissue;
iteratively adjusting delivery characteristics of the particles based on analysis until a predetermined success rate is achieved; and
delivering the drug in a bolus of many particles using adjusted delivery characteristics.

26. A system for determining one or more properties of a material, comprising:
a volume through which a particle can pass in a desired direction;
an optical component configured to provide a measurement light;
a detector positioned to detect light emanating from the particle in response to the measurement light, the detected light being modulated as the particle moves along a detection region within the volume, the detector configured to generate a time-varying signal in response to the detected light; and
an analyzer configured to receive the time-varying signal and determine a delivery success of the particle into the material and determine one or more properties of the material based upon characteristics of the time-varying signal.

* * * * *